US008287918B2

(12) United States Patent
Noguchi et al.

(10) Patent No.: US 8,287,918 B2
(45) Date of Patent: *Oct. 16, 2012

(54) MEDICAMENT FOR TREATING LUNG CANCER

(75) Inventors: Toshihiro Noguchi, Osaka (JP); Akemi Baba, Oklahoma City, OK (US)

(73) Assignee: Dainippon Sumitomo Pharma Co., Ltd., Osaka-Shi (JP)

( * ) Notice: Subject to any disclaimer, the term of this patent is extended or adjusted under 35 U.S.C. 154(b) by 137 days.

This patent is subject to a terminal disclaimer.

(21) Appl. No.: 12/637,667

(22) Filed: Dec. 14, 2009

(65) Prior Publication Data

US 2010/0092579 A1    Apr. 15, 2010

Related U.S. Application Data

(62) Division of application No. 10/466,491, filed as application No. PCT/JP02/00672 on Jan. 29, 2002, now Pat. No. 7,659,257.

(30) Foreign Application Priority Data

Jan. 30, 2001   (JP) .................................. 2001-22394

(51) Int. Cl.
*A01N 43/04*  (2006.01)
*A01N 59/16*  (2006.01)
*A61K 31/70*  (2006.01)
*A61K 33/24*  (2006.01)

(52) U.S. Cl. .......................................... 424/649; 514/34

(58) Field of Classification Search ........................ None
See application file for complete search history.

(56) References Cited

U.S. PATENT DOCUMENTS 4,673,668 A    6/1987   Ishizumi et al.

OTHER PUBLICATIONS

Takagi et al., Effects of 13-hydroxy SM5887 in combination with other anticancer agents on human tumor lines, Investigational New Drugs, 14:357-363, 1996.*
Yanagi et al., Abstract of the publication in Japanese Cancer Association, No. 2168, 1989.*
Takagi, T., et al., "Effects of 13-hydroxy SM5887 in combination with other anticancer agents on human tumor cell lines," Invest. New Drugs, vol. 14, pp. 357-363 (1996).
Hida, T., et al., "Cyclooxygenase-2 Inhibitor Induces Apoptosis and Enhances Cytotoxicity of Various Anticancer Agents in Non-Small Cell Lung Cancer Cell Lines," Clin. Cancer Res., vol. 6, pp. 2006-2011 (2000).
Ohe, Y., et al., "In Vitro Evaluation of the New Anticancer Agents KT6149, MX-2, SM5887, Menogarl, and Liblomycin Using Cisplatin- or Adriamycin-resistant Human Cancer Cell Lines," Cancer Research, vol. 49, pp. 4098-4102 (1989).
U.S. Appl. No. 10/466,491 Office Action dated Jul. 1, 2005.
U.S. Appl. No. 10/466,491 Office Action dated Feb. 24, 2006.
U.S. Appl. No. 10/466,491 Office Action dated Jan. 17, 2007.
U.S. Appl. No. 10/466,491 Office Action dated Sep. 21, 2007.
U.S. Appl. No. 10/466,491 Office Action dated Apr. 4, 2008.
U.S. Appl. No. 10/466,491 Office Action dated Jan. 28, 2009.
U.S. Appl. No. 10/466,491 Notice of Allowance dated Sep. 22, 2009.
Takagi, Tatsuyo et al., Investigational New Drugs, vol. 14, pp. 357-363, (1996).
Hida, Toyoaki et al., Clinical Cancer Research, vol. 6, pp. 2001-2006, (2000).
Ohe, Yuichiro et al, Cancer Research, vol. 49, pp. 4098-4102, (1989).
Kuffel, Mary J. et al., Cancer Chemother Pharmacol, vol. 30, pp. 51-57, (1992).
Suzuki, Tadashi et al., Investigational New Drugs, vol. 15, pp. 219-225, (1997).
The 48th Annual meeting of the Japanese Cancer Association, (1989), No. 2168, (English Translation attached).
Yamauchi, S. et al., Abstract of "Combination effects of amrubicin, a novel anthracycline, with cisplatin on human lung cancer cells", European Journal of Cancer, vol. 37, Apr. 2001, pp. S46.
Sumitomo, Abstract of "Amrubicin Hydrochloride", Drugs of the Future, vol. 22, No. 11, 1997, pp. 1271-1272.
Yamaoka, T. et al., Jpn. J. Cancer Res., vol. 89, Oct. 1998, pp. 1067-1073.
D.S. Ettinger, Seminars in Oncology, vol. 28, No. 2, Suppl. 4, Apr. 2001, pp. 27-29.
Takigawa, N. et al., Acta Med Okayama, vol. 46, No. 4, 1992, pp. 249-256.
S. Vogl et al., Cancer, vol. 38, Jul. 1976, pp. 21-26.
G. Colon-Otero et al., The Cancer Journal from Scientific American, vol. 3, No. 5, (Sep./Oct. 1997), pp. 297-302.
Mascaux, C. et al., "A systematic review of the role of etoposide and cisplatin in the chemotherapy of small cell lung cancer with methodology assessment and meta-analysis," Lung Cancer, vol. 30, 2000, pp. 23-36.
Office Action for Korean Patent Application No. 10-2010-7019541 issued on Nov. 23, 2010.
Communication from Japanese Patent Office in connection with the corresponding Japanese Patent Application, "Interrogation by Administrative Patent Judge dated Nov. 2, 2011," Pretrial Examiner Report, Appeal Trial No. 2010-006080, Application No. 2002-560654.
Katakami, Nobuyuki, "Treatment of Respiratory Disease Based on EBM, Advancement of Small Cell Lung Cancer Treatment," Modern Physician, Jan. 15, 21(1), p. 87-93, (2001).
Nakagawa, Kazuhiko, "Therapy Topics 100, New Therapy for Small Cell Lung Cancer," The Journal of Therapy, vol. 81, Extra Issue, p. 286-290 (1999).

* cited by examiner

*Primary Examiner* — Traviss C McIntosh, III

(74) *Attorney, Agent, or Firm* — Birch, Stewart, Kolasch & Birch, LLP

(57) ABSTRACT

Lung cancer can be treated effectively by combination of amrubicin or a pharmaceutically acceptable salt thereof with cisplatin.

11 Claims, 3 Drawing Sheets

MEDICAMENT FOR TREATING LUNG CANCER

This application is a Divisional of application Ser. No. 10/466,491 filed on Jul. 17, 2003, now U.S. Pat. No. 7,659,257, and for which priority is claimed under 35 U.S.C. §120. Application Ser. No. 10/466,491 is the national phase of PCT International Application No. PCT/PCT/JP2002/00672 filed on Jan. 29, 2002 under 35 U.S.C. §371. This application also claims priority of Application No. 2001-22394 filed in Japan on Jan. 30, 2001 under 35 U.S.C. §119.

TECHNICAL FIELD

The present invention relates to a medicament for treating lung cancer, comprising amrubicin or a pharmaceutically acceptable salt thereof as an active ingredient, for a use in combination with cisplatin.

BACKGROUND ART

Amrubicin ((+)-(7S,9S)-9-acetyl-9-amino-7-[(2-deoxy-β-D-erythro-pentopyranosyl)oxy]-7,8,9,10-tetrahydro-6,11-dihydroxy-5,12-naphthacenedione) is an anthracycline compound represented by the following chemical structural formula (JP-Hei3-5397B):

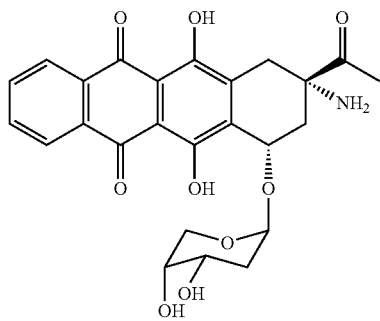

Amrubicin is easily reduced in vivo to form a metabolite (amrubicinol) which is a 13-hydroxylated product. This amrubicinol has a considerably stronger inhibitory activity against growth of tumor cells than that of amrubicin. Doxorubicin and daunomycin, other anthracycline compounds, also form reduced metabolites, which in contrast have reduced activities (Cancer Chemothr. Pharmacol., 30, 51-57 (1992)). Also for the cardiac toxicity, amrubicin is far weaker than doxorubicin in rabbit chronic experimental model (Invest. New Drug, 15, 219-225 (1997)).

It has been known that, although anthracycline compounds have similar structures, they are different in their indications, action mechanisms and so on as described below. Daunorubicin and idarubicin are approved for treatment of leukemia but are not approved for treatment of solid cancers. On the other hand, doxorubicin, epirubicin, pirarubicin and aclarubicin are approved for treatment of solid cancers (Drugs in Japan, 23rd. Ed., 2000, Jiho, Inc.). Daunorubicin and doxorubicin inhibit synthesis of DNA and synthesis of RNA in similar degrees but aclarubicin and marcellomycin inhibit synthesis of RNA more strongly than synthesis of DNA; therefore their mechanism of exerting antitumor activities are quite different (JJSHP, 27, 1087-1110 (1991)). It has been known that, in this manner, even if drugs belong to the same category of anthracycline, they have different effect depending on the kind of cancer, and the same anticancer agent has different effect depending on the kind of cancer. Consequently, it is necessary to specifically confirm by experiment whether or not a specific anticancer agent is effective against a specific tumor (cancer).

It has been described that amrubicin exhibits an additive effect by use in combination with another anticancer agent in vitro. (Investigational New Drugs, 14, 357-363 (1996)). For example, it has been described that a use of amrubicin hydrochloride in combination with cisplatin or the like exhibits an additive effect on human T-cell leukemia MOLT-3 cell strain and human osteosarcoma MG-63 cell strain. Additionally, an effect has been described, in an experiment with murine leukemia P388 cell strain, for a combined use of amrubicin and cisplatin in vivo (Yoshikazu YANAGI et al., Abstracts of publications in Japanese Cancer Association, No. 2168 (1989)). No report, however, has been described for a combined use of amrubicin and cisplatin against lung cancer.

Although cisplatin is an excellent anticancer agent, it has been known that it has also troublesome side effects such as nephrotoxicity and so on.

DISCLOSURE OF INVENTION

As the result of extensive studies, the present inventors have found the facts that lung cancers can be remarkably cured without increasing side effects observed in the single use of agents when amrubicin and cisplatin are used in combination, and that the side effects can be dramatically reduced when respective doses are decreased keeping the therapeutic effect in the combined use of amrubicin and cisplatin. Thus, the present invention has been completed.

The gist of the invention is as described below:

(1) A medicament for treating lung cancer, comprising amrubicin or a pharmaceutically acceptable salt thereof as an active ingredient, for a use in combination with cisplatin.

(2) The medicament for treating lung cancer as described in (1), wherein the lung cancer is small cell lung cancer, lung adenocarcinoma, squamous cell lung carcinoma or large cell lung carcinoma.

(3) The medicament for treating lung cancer as described in (1), wherein the lung cancer is small cell lung cancer.

(4) The medicament for treating lung cancer as described in any of (1) to (3), wherein the active ingredient is amrubicin hydrochloride.

(5) The medicament for treating lung cancer as described in any of (1) to (4), which is administered simultaneously with, separately from or sequentially with cisplatin.

(6) The medicament for treating lung cancer as described in any of (1) to (5), comprising amrubicin or a pharmaceutically acceptable salt thereof as an active ingredient, for a patient carrying a lung cancer to which cisplatin has been administered or is planned to be administered.

(7) The medicament for treating lung cancer for a use in combination with cisplatin as described in any of (1) to (6), which is packaged such that about 60 to about 135 mg/m² of amrubicin or a pharmaceutically acceptable salt thereof is administered in a single dose or in 2 to 5 divided doses.

(8) The medicament for treating lung cancer as described in (7), which is packaged such that about 110 to about 130 mg/m² of amrubicin or a pharmaceutically acceptable salt thereof is administered in a single dose.

(9) The medicament for treating lung cancer as described in (7), which is packaged such that about 25 to about 50 mg/m² of amrubicin or a pharmaceutically acceptable salt thereof is administered once a day for 3 days.

(10) The medicament for treating lung cancer as described in (7), which is packaged such that about 35 to about 45 mg/m² of amrubicin or a pharmaceutically acceptable salt thereof is administered once a day for 3 days.

(11) The medicament for treating lung cancer as described in (9) or (10), wherein amrubicin or a pharmaceutically acceptable salt thereof is administered for continuous 3 days.

(12) The medicament for treating lung cancer as described in any of (7) to (11), wherein about 35 to about 90 mg/m² of cisplatin to be used in combination is administered in a single dose.

(13) The medicament for treating lung cancer as described in any of (7) to (11), wherein about 50 to about 70 mg/m² of cisplatin to be used in combination is administered in a single dose.

(14) The medicament for treating lung cancer as described in any of (1) to (13), comprising amrubicin or a pharmaceutically acceptable salt thereof as an active ingredient, for a patient having a lung cancer, wherein the patient is one having failed to continue receiving the treatment with cisplatin because of side effects, and wherein the patient is receiving administration of cisplatin in an amount that will cause reduced side effect.

(15) A use of amrubicin or a pharmaceutically acceptable salt thereof for the manufacture of a medicament for treating lung cancer to be used in combination with cisplatin.

(16) A method for treating a lung cancer which comprises administering amrubicin or a pharmaceutically acceptable salt thereof and cisplatin.

BEST MODE FOR CARRYING OUT THE INVENTION

Figure 1:
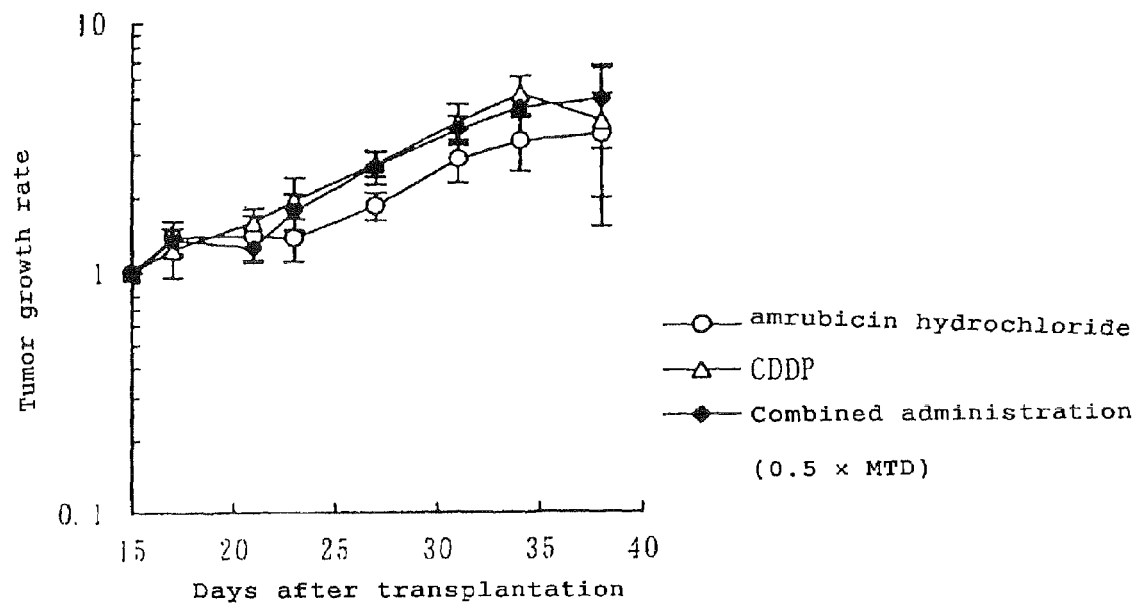
FIG. 1 shows an inhibitory effect of growth of small cell lung cancer cell when 0.5 times of the maximum tolerated dose (MTD) of amrubicin hydrochloride and 0.5 times of the maximum tolerated dose of cisplatin are used in combination. ○ denotes an amrubicin hydrochloride alone administration group, Δ denotes a cisplatin (CDDP) alone administration group and ♦ denotes a combined administration group.

The medicament for treating lung cancer of the invention is a medicament for treating lung cancer comprising amrubicin or a pharmaceutically acceptable salt thereof as an active ingredient and is used in combination with cisplatin.

Amrubicin or pharmaceutically acceptable salts thereof can be prepared, for example, according to J. Org. Chem., 52, 4477-4485 (1987). The pharmaceutically acceptable salts of amrubicin include acid addition salts and base addition salts. The acid addition salts include, for example, inorganic acid salts such as hydrochloride, hydrobromide, sulfate, hydroiodide, nitrate, phosphate and the like; and organic acid salts such as citrate, oxalate, acetate, formate, propionate, benzoate, trifluoroacetate, fumarate, maleate, tartrate, aspartate, glutamate, methanesulfonate, benzenesulfonate, camphorsulfonate and the like. The base addition salts include, for example, inorganic base addition salts such as sodium salt, potassium salt, calcium salt, magnesium salt, ammonium salt and the like; and organic base addition salts such as triethylammonium salt, triethanolammonium salt, pyridinium salt, diisopropylammonium salt and the like. Preferred pharmaceutically acceptable salts include hydrochloride and the like.

Cisplatin (cis-diammin dichloroplatinum) can be prepared, for example, according to Ann., 51, 1 (1845).

The maximum tolerated dose of amrubicin or pharmaceutically acceptable salts thereof is, referring to amrubicin hydrochloride, 25 mg/kg (75 mg/m²) for mice and 130 mg/m² for humans in once a day single dose, and 50 mg/m² per day for administration in 3 continuous days. The maximum tolerated dose of cisplatin is 10 mg/kg (30 mg/m²) for mice and 90 mg/m² for humans.

The lung cancer includes, for example, small cell lung cancer, lung adenocarcinoma, squamous cell lung carcinoma, large cell lung carcinoma, carcinoids, adenoid cystic carcinoma, mucoepidermoid carcinoma, malignant mixed tumor and the like. Among them, examples in which the medicament for treating lung cancer of the invention exhibit preferred effect include small cell lung cancer, lung adenocarcinoma, squamous cell lung carcinoma, large cell lung carcinoma and the like, and particularly preferred one is small cell lung cancer.

From results of Example 1 with mice, the following facts are found:

(1) In a combined use of 0.5 times of the maximum tolerated dose (12.5 mg/kg) of amrubicin hydrochloride and 0.5 times of the maximum tolerated dose (5 mg/kg) of cisplatin, an anticancer effect was observed at a similar level as compared with those found in groups in which the maximum tolerated dose of each of respective agents was administered independently. On the other hand, the side effects of cisplatin were significantly decreased.

(2) In a combined use of 0.8 times or 1.0 time of the maximum tolerated dose (20 or 25 mg/kg) of amrubicin hydrochloride and 0.8 times or 1.0 time of the maximum tolerated dose (8 or 10 mg/kg) of cisplatin, a stronger anticancer effect was observed as compared with those found in groups to which the maximum tolerated dose of each of respective agents was administered independently. On the other hand, the side effects of cisplatin were not increased but at a similar level.

As described above, by the combined use of about 0.5 to about 1 time of the maximum tolerated dose of amrubicin or a pharmaceutically acceptable salt thereof and about 0.5 to about 1 time of the maximum tolerated dose of cisplatin, anticancer effect can be obtained safely and sufficiently without increasing side effects of cisplatin and amrubicin or pharmaceutically acceptable salts thereof or sometimes decreasing the side effects. For example, when the side effects of cisplatin or amrubicin are taken up as a problem, a lower dose within the range of about 0.5 to about 1 time of the maximum tolerated dose of amrubicin or a pharmaceutically acceptable salt thereof and about 0.5 to about 1 time of the maximum tolerated dose of cisplatin can be applied; on the other hand, when the side effects of cisplatin or amrubicin are not taken up as a problem, a higher dose within a range of about 0.5 to about 1 time of the maximum tolerated dose of amrubicin or a pharmaceutically acceptable salt thereof and about 0.5 to about 1 time of the maximum tolerated dose of cisplatin can be used for safely obtaining the maximum anticancer effect.

In the combined use of amrubicin or a pharmaceutically acceptable salt thereof and cisplatin, the dose of cisplatin can be within a range of about 0.5 to about 1 time of the maximum tolerated dose of cisplatin, and specifically it can be about 0.5 times, about 0.8 times, about 1 time and the like. For example, when about 0.5 times of the maximum tolerated dose of cisplatin is administered, the dose of amrubicin or a pharmaceutically acceptable salt thereof can be within a range of about 0.5 to about 1.0 time of its maximum tolerated dose, and more preferably, can be about 0.8 times or about 1 time. When about 0.8 times of the maximum tolerated dose of cisplatin is administered, the dose of amrubicin or a pharmaceutically acceptable salt thereof can be within a range of about 0.5 to about 1 time of its maximum tolerated dose, and more preferably, can be about 0.8 times or about 1 time. Moreover, cisplatin can be administered in an amount of about 1 time of the maximum tolerated dose.

In the treatment of human lung cancers, while the amount may be suitably varied depending on conditions, age, body weight and so on of the patient, about 60 to about 135 mg/m$^2$ of amrubicin or a pharmaceutically acceptable salt thereof and about 35 to about 90 mg/m$^2$ of cisplatin, for example, can be used in combination. Amrubicin or a pharmaceutically acceptable salt thereof can be administered, for example, in an amount of about 60 to about 135 mg/m$^2$ in a single dose or in 2 to 5 divided doses. Preferred schedule for administration of amrubicin or a pharmaceutically acceptable salt thereof includes, for example, a single administration, once daily administration for 3 days and the like, and includes most preferably once daily administration over 3 continuous days. The dose for a single administration includes, for example, a range of about 110 to about 130 mg/m$^2$, and includes most preferably about 120 mg/m$^2$ and the like. The dose per day for administration over 3 continuous days includes, for example, a range of about 25 to about 50 mg/m$^2$, preferably a range of about 35 to 45 mg/m$^2$ and the like, and includes most preferably about 40 mg/m$^2$, about 45 mg/m$^2$ and the like.

The amount of administration of cisplatin to be administered in combination includes, for example, a range of about 35 to about 90 mg/m$^2$ for a single administration, and preferably about 50 mg/m$^2$ to about 80 mg/m$^2$ for a single administration. Specifically, it includes about 60 mg/m$^2$, about 80 mg/m$^2$ and the like, and includes, as a most preferable example, about 60 mg/m$^2$ and the like. In addition, cisplatin can be administered in several divided doses, daily or over several days.

In patients carrying a lung cancer treated with cisplatin, when it has been judged that the treatment can not be continued because of side effects, a treatment with decreased side effects of cisplatin can be continued by an administration of cisplatin in a dose with reduced side effects and additional administration of amrubicin or a pharmaceutically acceptable salt thereof. The dose of cisplatin for reduction of side effects includes, for example, a range of about 35 to about 70 mg/m$^2$ and preferably includes a range of about 35 to about 60 mg/m$^2$.

Examples of the combination of amounts to be administered of amrubicin or a pharmaceutically acceptable salt thereof and cisplatin include the followings:

| Amrubicin or pharmaceutically acceptable salt thereof | Cisplatin |
|---|---|
| About 60 mg/m$^2$ (single dose) | About 35 mg/m$^2$ (single dose) |
| About 120 mg/m$^2$ (single dose) | About 80 mg/m$^2$ (single dose) |
| About 25 mg/m$^2$ (once a day) × 3 days | About 35 mg/m$^2$ (single dose) |
| About 40 mg/m$^2$ (once a day) × 3 days | About 60 mg/m$^2$ (single dose) |
| About 40 mg/m$^2$ (once a day) × 3 days | About 80 mg/m$^2$ (single dose) |
| About 45 mg/m$^2$ (once a day) × 3 days | About 60 mg/m$^2$ (single dose) |
| About 45 mg/m$^2$ (once a day) × 3 days | About 80 mg/m$^2$ (single dose) |

In the medicament for treating lung cancer of the invention, amrubicin or a pharmaceutically acceptable salt thereof is administered simultaneously with, separately from or sequentially with cisplatin. When it is administered separately or sequentially, amrubicin or a pharmaceutically acceptable salt thereof may be administered before or be administered after cisplatin. The interval of both administration can suitably be set and may be, for example, 1 to several hours, ten to several tens hours, 1 to several days, 1 week and the like. For example, it is preferred, in view of patient's convenience such as visiting hospital or the like, that amrubicin or a pharmaceutically acceptable salt thereof and that of cisplatin are administered on the same day.

While the administration of the medicament for treating lung cancer of the invention suitably varies depending on conditions, age and body weight of patient, form for administration, amount for administration of cisplatin to be administered in combination, frequency of administration and the like, it is preferred that the both administrations are repeated after the administration of the above amrubicin or a pharmaceutically acceptable salt thereof and that of cisplatin at an interval of about 7 days to about 60 days. Most preferably, repetition is made at an interval of about 2 weeks to about 4 weeks and further preferably at an interval of about 3 weeks.

Amrubicin or a pharmaceutically acceptable salt thereof can usually be administered parenterally (for example, intravenous, intraarterial, subcutaneous or intramuscular injection; intravesially, intraperitoneally, intrapleurally, topically, rectally, percutaneously, nasally and so on). Preferred route includes intravenous injection. In addition, oral administration is also possible, and forms for oral administration include tablets, capsules, pills, granules, powders, solutions, syrups, suspensions and the like.

Cisplatin can usually be administered parenterally (for example, intravenous, intraarterial, subcutaneous or intramuscular injection; intravesially, intraperitoneally, intrapleurally, topically, rectally, percutaneously, nasally and so on). Preferred route includes intravenous injection. In addition, oral administration is also possible, and forms for oral administration include tablets, capsules, pills, granules, powders, solutions, syrups, suspensions and the like.

In the medicament for treating lung cancer of the invention, other anticancer agent, irradiation therapy, surgical measures and the like can further be combined. Additionally, it can be in the form of a kit for combined medicament for treating lung cancer comprising (a) a first composition comprising amrubicin or a pharmaceutically acceptable salt thereof as an active ingredient and (b) a second composition comprising cisplatin as an active ingredient.

EXAMPLES

The invention is described below in more detail with reference to Examples, which do not limit the invention.

Example 1

Antitumor Activity by a Combination of Amrubicin Hydrochloride and Cisplatin

Human small cell lung cancer LX-1 cell strain was subcutaneously transplanted to nude mice (80 animals) at 5 weeks of age. After 15 days from the tumor transplantation, 36 animals having a tumor volume of about 200 to 500 mm$^3$ were allotted to 6 groups consisting of 6 animals per group. On the same day, the animals received intravenous administration, respectively, of physiological saline for "vehicle group", the maximum tolerated dose of amrubicin hydrochloride (25 mg/kg) for "an amrubicin hydrochloride alone administration group", the maximum tolerated dose of cisplatin (10 mg/kg) for "cisplatin alone administration group", 0.5 times of the maximum tolerated dose of amrubicin hydrochloride and 0.5 times of the maximum tolerated dose of cisplatin for "combined administration group (0.5×MTD)", 0.8 times of the maximum tolerated dose of amrubicin hydrochloride and 0.8 times of the maximum tolerated dose of cisplatin for "combined administration group (0.8×MTD)", the maximum tolerated dose of amrubicin hydrochloride and the maximum tolerated dose of cisplatin for "combined administration group (1×MTD)". Thereafter, tumor volume and body weight of the mice were measured for 23 days.

Amrubicin hydrochloride was dissolved in a cysteine buffer (containing 0.4 mg/ml L-cysteine hydrochloride monohydrate and 6.25 mg/ml lactose) to give a solution of 2.5 mg/ml, which was diluted with a physiological saline to give solutions of 2.0 and 1.25 mg/ml. Each 10 ml/kg aliquot of the solutions was administered as the maximum tolerated dose, the 0.8 times dose or the 0.5 times dose of amrubicin hydrochloride.

Cisplatin was administered by giving 20, 16 or 10 ml/kg aliquot of Randa Injection (containing 0.5 mg/ml), purchased from Nippon Kayaku Co., Ltd., as the maximum tolerated dose, the 0.8 times dose or the 0.5 times dose of cisplatin.

Figure 2:
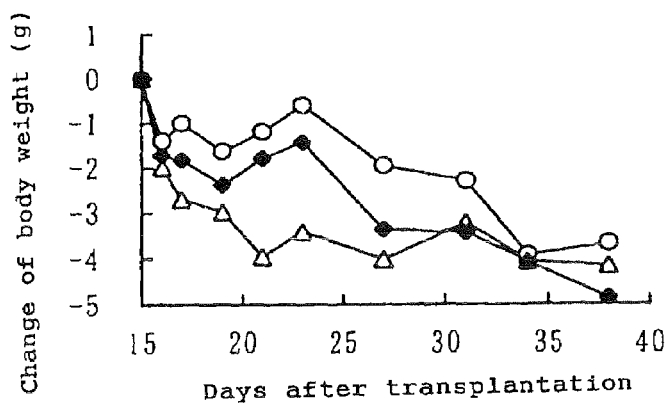
FIG. 2 shows a reducing effect of the body weight as a side effect when 0.5 times of the maximum tolerated dose of amrubicin hydrochloride and 0.5 times of the maximum tolerated dose of cisplatin are used in combination. ○ denotes an amrubicin hydrochloride alone administration group, Δ denotes a cisplatin alone administration group and ♦ denotes a combined administration group.

FIGS. 1 and 2 show changes in tumor volume and body weight for the combined administration (0.5×MTD) group together with data for the amrubicin hydrochloride alone administration group and those for the cisplatin alone administration group.

Figure 3:
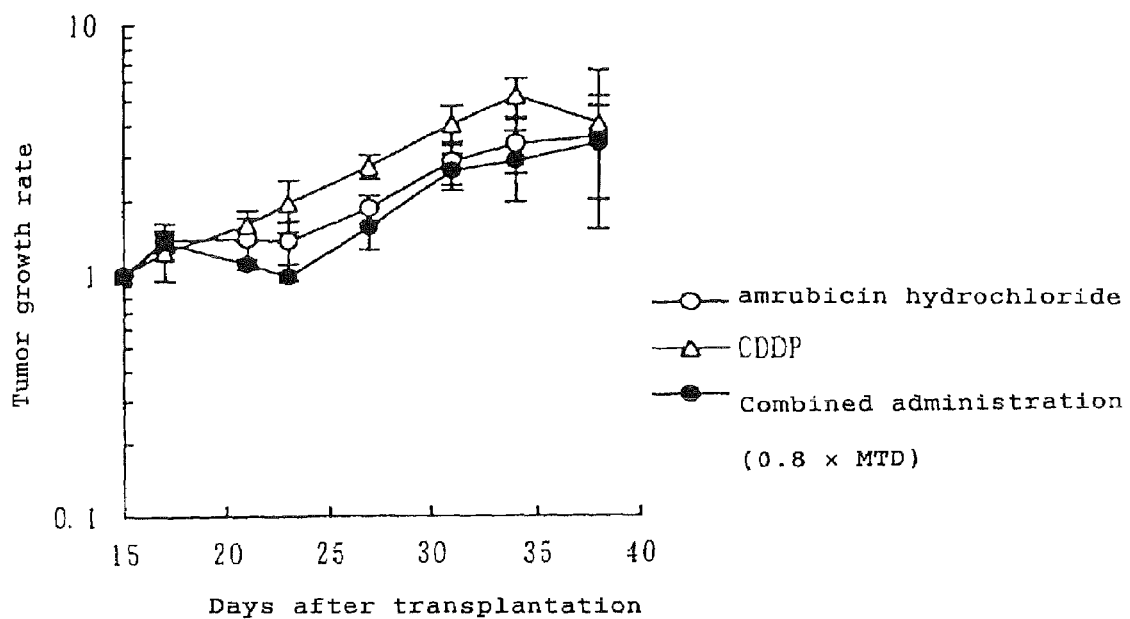
FIG. 3 shows an inhibitory effect of growth of small cell lung cancer cell when 0.8 times of the maximum tolerated dose of amrubicin hydrochloride and 0.8 times of the maximum tolerated dose of cisplatin are used in combination. ○ denotes an amrubicin hydrochloride alone administration group, Δ denotes a cisplatin alone administration group and ● denotes a combined administration group.
Figure 4:
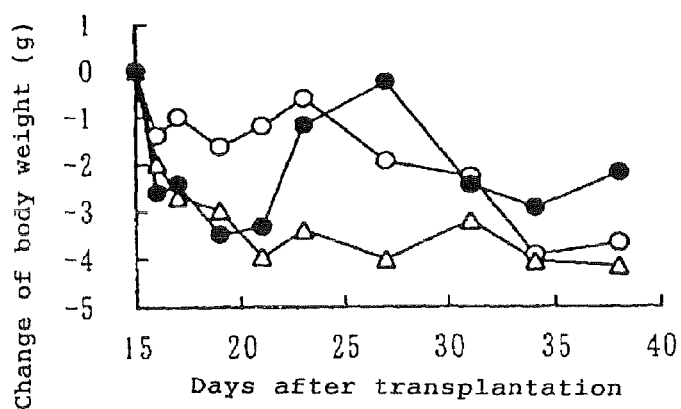
FIG. 4 shows a reducing effect of the body weight as a side effect when 0.8 times of the maximum tolerated dose of amrubicin hydrochloride and 0.8 times of the maximum tolerated dose of cisplatin are used in combination. ○ denotes an amrubicin hydrochloride alone administration group, Δ denotes a cisplatin alone administration group and ● denotes a combined administration group.

FIGS. 3 and 4 show changes in tumor volume and body weight for the combined administration (0.8×MTD) group together with data for the amrubicin hydrochloride independent administration group and those for the cisplatin independent administration group.

Figure 5:
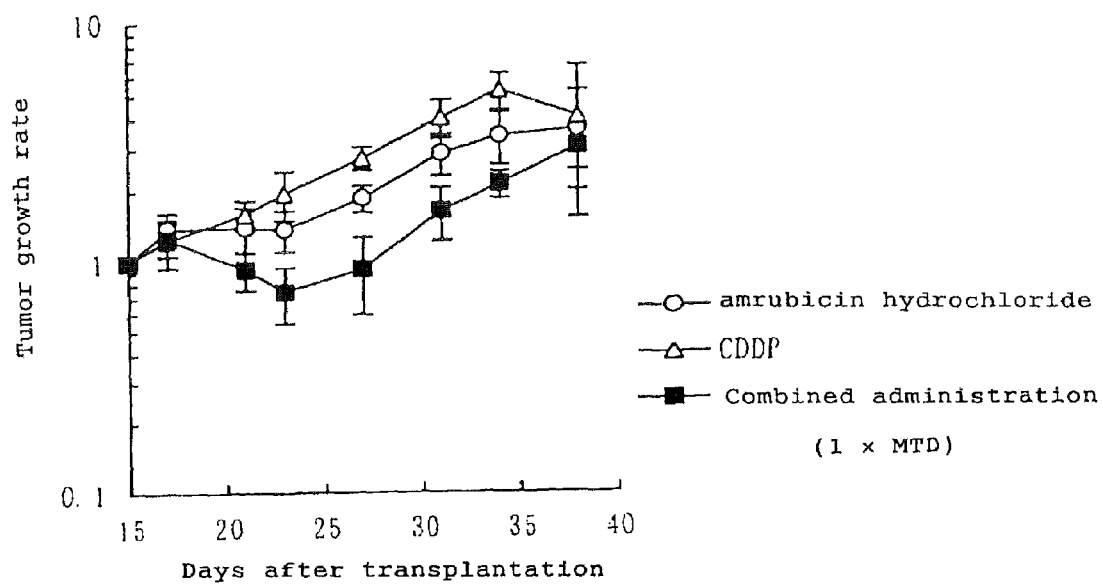
FIG. 5 shows an inhibitory effect of growth of small cell lung cancer cell when 1.0 time of the maximum tolerated dose of amrubicin hydrochloride and 1.0 time of the maximum tolerated dose of cisplatin are used in combination. ○ denotes an amrubicin hydrochloride alone administration group, Δ denotes a cisplatin alone administration group and ■ denotes a combined administration group.
Figure 6:
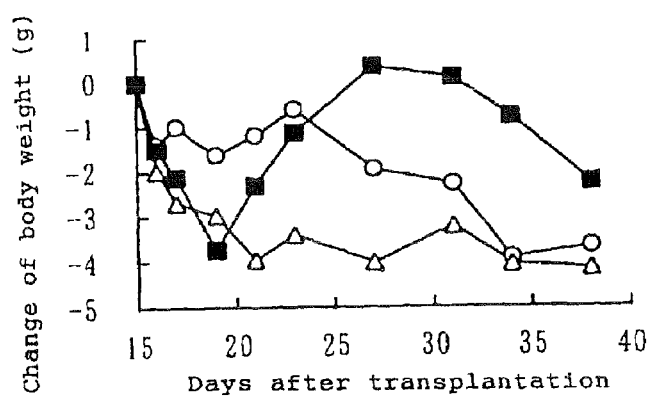
FIG. 6 shows a reducing effect of the body weight as a side effect when 1.0 time of the maximum tolerated dose of amrubicin hydrochloride and 1.0 time of the maximum tolerated dose of cisplatin are used in combination. ○ denotes an amrubicin hydrochloride alone administration group, Δ denotes a cisplatin alone administration group and ■ denotes a combined administration group.

FIGS. 5 and 6 show changes in tumor volume and body weight for the combined administration (1×MTD) group together with data for the amrubicin hydrochloride alone administration group and those for the cisplatin alone administration group.

TABLE 1 shows the minimum T/C % of tumor growth rate in respective groups. The minimum T/C % was calculated as follows:

Minimum T/C %: the minimum value of ratio (%) of tumor growth rate[*] for respective administration groups to tumor growth rate[*] for the vehicle administration group within the period for measurement.

[*] Tumor growth rate: a ratio of an average value of tumor volume for a group of 6 animals at respective point in time of measurement to an average value of tumor volume for a group of 6 animals at respective point in time of drug administration.

TABLE 1

| Administration group | Minimum T/C % |
| --- | --- |
| Maximum tolerated dose amrubicin hydrochloride administration group | 55 |
| Maximum tolerated dose cisplatin administration group | 68 |
| Maximum tolerated dose amrubicin hydrochloride plus maximum tolerated dose cisplatin combined administration group | 30 |
| 0.8 Times of maximum tolerated dose amrubicin hydrochloride plus 0.8 times of maximum tolerated dose cisplatin combined administration group | 40 |
| 0.5 Times of maximum tolerated dose amrubicin hydrochloride plus 0.5 times of the maximum tolerated dose cisplatin combined administration group | 54 |

1. Results in the Combined Administration (0.5×MTD) Group:

As shown in FIG. 1, the antitumor effect in the combined administration was a similar effect as compared with those in the maximum tolerated dose administration groups for respective single agents. Thus, the minimum T/C % was 55% in the amrubicin hydrochloride alone administration group, 68% in cisplatin alone administration group and 54% in the combined administration (0.5×MTD) group.

For the side effects as evaluated by loss in the body weight of animals, as shown in FIG. 2, a remarkable reducing effect of the side effects, possibly caused by halving the dose of cisplatin, was observed as compared with single administration groups for respective single agents.

2. Results in the Combined Administration (0.8×MTD) Group:

As shown in FIG. 3, there was a reduction of tumor, and the antitumor effect in the combined administration was a stronger antitumor effect as compared with those in the single administration groups for respective single agents. Thus, the minimum T/C % was 55% in the amrubicin hydrochloride alone administration group, 68% in cisplatin alone administration group and 40% in the combined administration (0.8×MTD) group.

The side effects as evaluated by loss in the body weight of animals, as shown in FIG. 4, was at a similar degree to those in the cisplatin alone administration group.

3. Results in the Combined Administration (1×MTD) Group:

As shown in FIG. 5, there was a reduction of tumor as in the case of 0.8 time administration, and the antitumor effect in the combined administration was a stronger antitumor effect as compared with those in the single administration groups for respective single agents. Thus, the minimum T/C % was 55% in the amrubicin hydrochloride alone administration group, 68% in cisplatin alone administration group and 30% in the combined administration (1×MTD) group.

For the side effects as evaluated by loss in the body weight of animals, as shown in FIG. 6, there was a transitory loss in the body weight by about 3 g, but the weight recovered and the side effects was at a similar degree to those in the maximum tolerated dose administration groups for cisplatin as a single agent.

As described above, side effects were reduced and remarkable therapeutic effects were observed in the combined administration of amrubicin hydrochloride and cisplatin. In addition, as it can be understood from FIGS. 1 to 6, the effects by the combined use appear with particular significance during 2 weeks from the administration and the effects almost disappear after 3 weeks. Consequently, it is preferred that the administration be repeated again after about 2 weeks to about 4 weeks, and particularly, re-administration is carried out after 3 weeks and continued thereafter.

Example 2

Fluctuation Analysis for Expression of Carbonyl Reductase Gene in Normal and Tumor Tissues DNA chip analysis was conducted using total RNAs prepared with 69 samples from human lung normal tissue, and 44 samples from lung adenocarcinoma, 32 samples from squamous cell lung carcinoma, 5 samples from large cell lung carcinoma and 18 samples from leukemia cell. The DNA chip analysis was carried out with Gene Chip Human Genome U95 A, B, C, D and E from Affymetrix. Specifically, the analysis was performed with a procedure consisting of (1) preparation of a cDNA from a total RNA, (2) preparation of a labeled cRNA from said cDNA, (3) fragmentation of the labeled cRNA, (4) hybridization of the fragmented cRNA with a probe array, (5) staining of the probe array, (6) scanning of the probe array and (7) analysis of gene expression.

(1) Preparation of a cDNA from a Total RNA:

Each of 11 µl of mixed solutions containing 10 µg of each of total RNAs prepared with 69 samples from human lung normal tissue, and 44 samples from lung adenocarcinoma, 32 samples from squamous cell lung carcinoma, 5 samples from large cell lung carcinoma and 18 samples from leukemia cell and 100 pmols of T7-(dT) 24 primer (manufactured by Amersham) was heated at 70° C. for 10 minutes and cooled on ice. After cooling, 4 µl of 5× First Strand cDNA Buffer contained in SuperScript Choice System for cDNA Synthesis (manufactured by Gibco-BRL), 2 µl of 0.1 M DTT (dithiothreitol) contained in said kit and 1 µl of 10 mM dNTP Mix were added and the mixture was heated at 42° C. for 2 minutes. Further, 2 µl (400 U) of SuperScript II RT contained in said kit was added. The mixture was heated at 42° C. for 1 hour and cooled on ice. After cooling, 91 µl of DEPC treated water (manufactured by Nacalai Tesque, Inc.), 30 µl of 5× Second Strand Reaction Buffer contained in said kit, 3 µl of 10 mM dNTP Mix, 1 µl (10 U) of $E.\ coli$ DNA Ligase contained in said kit, 4 µl (40 U) of $E.\ coli$ DNA Polymerase I contained in said kit and 1 µl (2 U) of $E.\ coli$ RNAaseH contained in said kit were added and reacted at 16° C. for 2 hours. Then, after adding 2 µl (10 U) of T4 DNA Polymerase contained in said kit and reacting at 16° C. for 5 minutes, 10 µl of 0.5 M EDTA was added. Then, 162 µl of phenol/chloroform/isoamyl alcohol solution (manufactured by Nippongene) was added and mixed. The mixed solution was transferred to Phase Lock Gel Light (manufactured by Eppendorf), which was previously centrifuged at room temperature and 14,000 rpm for 30 seconds, centrifuged at room temperature and 14,000 rpm for 2 minutes and 145 µl of aqueous layer was transferred to an Eppendorf tube. To the obtained solution were added 72.5 µl of 7.5 M ammonium acetate solution and 362.5 µl of ethanol, and after mixing, the mixture was centrifuged at 4° C. and 14,000 rpm for 20 minutes. After centrifugation, the supernatant was discarded to give a DNA pellet containing the prepared cDNA. Then, 0.5 ml of 80% ethanol was added to said pellet and the mixture was centrifuged at 4° C. and 14,000 rpm for 5 minutes. The supernatant was discarded. After repeating again the same treatment, the pellet was dried and dissolved in 12 µl of DEPC treated water.

By the above procedure, cDNAs were obtained from total RNAs derived from 69 samples from human lung normal tissue, and 44 samples from lung adenocarcinoma, 32 samples from squamous cell lung carcinoma, 5 samples from large cell lung carcinoma and 18 samples from leukemia cell.

(2) Preparation of a Labeled cRNA from Said cDNA:

To 5 µl of each of the cDNA solutions prepared in the above (1) were mixed 17 µl of DEPC treated water, 4 µl of 10×HY Reaction Buffer contained in BioArray High Yield RNA Transcript Labeling Kit (manufactured by ENZO), 4 µl of 10× Biotin Labeled Ribonucleotides contained in said kit, 4 µl of 10×DTT contained in said kit, 4 µl of 10× RNase Inhibitor Mix contained in said kit and 2 µl of 20×T7 RNA Polymerase contained in said kit, and reacted at 37° C. for 5 hours. After the reaction, 60 µl of DEPC treated water was added to the reaction solution and the prepared labeled cRNAs were purified with RNeasy Mini Kit according to the attached protocol.

(3) Fragmentation of the Labeled cRNA:

To a solution containing 20 µg of each of labeled cRNAs purified in the above (3) were added 8 µl of 5× Fragmentation Buffer (200 mM tris-acetate, pH 8.1 (manufactured by Sigma), 500 mM potassium acetate (manufactured by Sigma) and 150 mM magnesium acetate (manufactured by Sigma)). After heating 40 µl of the obtained reaction solution at 94° C. for 35 minutes, the solution was placed in ice. This allowed fragmentation of the labeled cRNAs.

(4) Hybridization of the Fragmented cRNA with a Probe Array:

To 40 µl of each of the fragmented cRNAs obtained in the above (3) were mixed 4 µl of 5 nM Control Oligo B2 (manufactured by Amersham), 4 µl of 100× Control cRNA Cocktail, 40 µl of Herring sperm DNA (manufactured by Promenga), 200 µl of Acetylated BSA (manufactured by Gibco-BRL), 200 µl of 2×MES Hybridization Buffer (200 mM MES, 2 M [Na$^+$], 40 mM EDTA, 0.02% Tween 20 (manufactured by Pierce), pH 6.5-6.7) and 144 µl of DEPC treated water to give 400 µl hybridized cocktail. Each of the obtained hybridized cocktails was heated at 99° C. for 5 minutes, and additionally at 45° C. for 5 minutes. After heating, the cocktail was centrifuged at room temperature and 14,000 rpm for 5 minutes to give a supernatant of the hybridized cocktail.

On the other hand, after rotating Human genome U95 probe array (manufactured by Affymetrix) filled with 1×MES hybridization buffer in a hybridization oven at 45° C. and 60 rpm for 10 minutes, 1×MES hybridization buffer was removed to give a probe array. To the probe array was added 200 µl of the supernatant of the hybridized cocktail obtained above, and the mixture was rotated in a hybridization oven at 45° C. and 60 rpm for 16 hours to give a probe array hybridized with fragmented cRNA.

(5) Staining of the Probe Array:

After collecting and removing the hybridized cocktail from each of the already hybridized probe array obtained in the above (4), the product was filled with Non-Stringent Wash Buffer (6×SSPE (prepared by diluting 20×SSPE (manufactured by Nacalai Tesque)), 0.01% Tween 20 and 0.005% Antifoam 0-30 (manufactured by Sigma)). Then, the fragmented cRNA and hybridized probe array were placed in respective positions of GeneChip Fluidics Station 400 (manufactured by Affymetrix) set with Non-Stringent Wash Buffer and Stringent Wash Buffer (100 mM MES, 0.1 M NaCl and 0.01% Tween 20). Then according to the staining protocol EuKGE-WS2, staining was carried out with a first staining solution (10 μl g/ml Streptavidin Phycoerythrin (SAPE) (manufactured by Molecular Probe), 2 mg/ml Acetylated BSA, 100 mM MES, 1 M NaCl (manufactured by Ambion), 0.05% Tween 20 and 0.005% Antifoam 0-30) and a second staining solution (100 μg/ml Goat IgG (manufactured by Sigma), 3 μg/ml Biotinylated Anti-Streptavidin antibody (manufactured by Vector Laboratories), 2 mg/ml Acetylated BSA, 100 mM MES, 1 M NaCl, 0.05% Tween 20 and 0.005% Antifoam 0-30).

(6) Scanning of the Probe Array and (7) Analysis of Gene Expression:

Each of probe arrays stained in the above (5) was subjected to HP GeneArray Scanner (manufactured by Affymetrix) to read the staining pattern.

Expression of carbonyl reductase 1 gene on the probe array was analyzed with GeneChip Workstation System (manufactured by Affymetrix) based on the staining pattern. Then, normalization and comparative analysis of gene expression were preformed according to the analysis protocol.

As the result, it was found that the expression frequency of carbonyl reductase 1 was 11% (2 cases in 18 cases) and median of expression abundance in human leukemia cell was −39, indicating that the gene is hardly expressed. On the other hand, it was found that the expression frequency of carbonyl reductase 1 in human tissues was 55% (24 cases in 44 cases), 63% (20 cases in 32 cases), 40% (2 cases in 5 cases) and 32% (22 cases in 69 cases) in adenocarcinoma, squamous cell carcinoma, large cell carcinoma and normal tissue, respectively, and expression abundance was 51, 96, 34 and 22, respectively, indicating that the expression of carbonyl reductase 1 was enhanced in lung cancer tissues as compared with the lung normal tissue and, particularly, the expression abundances in lung adenocarcinoma and squamous cell carcinoma were 2 times and 4 times that in lung normal tissue.

INDUSTRIAL APPLICABILITY

According to the invention, medicament for treating lung cancer combined amrubicin hydrochloride with cisplatin useful in the treatment of a subject of lung cancer is provided. By the combined use with cisplatin, the antitumor therapeutic effect of amrubicin hydrochloride can be improved and cancer therapy with reduced side effects of cisplatin becomes possible.

The invention claimed is:

1. A kit comprising:
   (1) a first composition comprising amrubicin or a pharmaceutically acceptable salt thereof;
   (2) a second composition comprising cisplatin wherein the first composition is adapted for once daily administration for 3 days of about 25 to about 50 mg/m² of amrubicin, or a pharmaceutically acceptable salt thereof; and the second composition is adapted for a single administration of about 35 to 90 mg/m² of cisplatin.

2. The kit of claim 1, wherein the first composition is adapted for once daily administration for 3 days of about 35 to about 45 mg/m² of amrubicin, or a pharmaceutically acceptable salt thereof.

3. The kit of claim 2, wherein the first composition is adapted for once daily administration for 3 days of about 40 mg/m² of amrubicin, or a pharmaceutically acceptable salt thereof.

4. The kit of claim 1, the second composition is adapted for a single administration of about 50 to about 80 mg/m² of cisplatin.

5. The kit of claim 4, the second composition is adapted for a single administration of about 60 mg/m² of cisplatin.

6. A kit comprising:
   (1) a first composition comprising amrubicin or a pharmaceutically acceptable salt thereof;
   (2) a second composition comprising cisplatin wherein the first composition is adapted for a single administration of about 60 to about 135 mg/m² of amrubicin, or a pharmaceutically acceptable salt thereof, and the second composition is adapted for a single administration of about 35 to 90 mg/m² of cisplatin.

7. The kit of claim 6, wherein the first composition is adapted for a single administration of about 110 to about 130 mg/m² of amrubicin, or a pharmaceutically acceptable salt thereof.

8. The kit of claim 7, the first composition is adapted for a single administration of about 120 mg/m² of amrubicin, or a pharmaceutically acceptable salt thereof.

9. The kit of claim 6, the second composition is adapted for a single administration of about 50 to about 80 mg/m² of cisplatin.

10. The kit of claim 9, the second composition is adapted for a single administration of about 60 mg/m² of cisplatin.

11. The kit according to any one of claims 1, 6-10 and 2-5, wherein the pharmaceutically acceptable salt of amrubicin is amrubicin hydrochloride.

* * * * *